US010085927B2

(12) United States Patent
Benabdillah et al.

(10) Patent No.: US 10,085,927 B2
(45) Date of Patent: *Oct. 2, 2018

(54) NONDETERGENT COSMETIC COMPOSITIONS COMPRISING AT LEAST ONE ALKOXYSILANE AND AT LEAST ONE MICROBIAL GUM AND STYLING USES

(75) Inventors: Katarina Benabdillah, Saint Jean du Pin (FR); Patrice Lerda, Asnieres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/697,483

(22) Filed: Feb. 1, 2010

(65) Prior Publication Data

US 2010/0254932 A1 Oct. 7, 2010

Related U.S. Application Data

(60) Provisional application No. 61/154,861, filed on Feb. 24, 2009.

(30) Foreign Application Priority Data

Jan. 30, 2009 (FR) .................................... 09 50604

(51) Int. Cl.
   *A61K 8/58* (2006.01)
   *A61K 8/73* (2006.01)
   *A61Q 5/12* (2006.01)
   *A61Q 5/06* (2006.01)

(52) U.S. Cl.
   CPC ............... *A61K 8/585* (2013.01); *A61K 8/73* (2013.01); *A61Q 5/06* (2013.01); *A61Q 5/12* (2013.01); *A61K 2800/88* (2013.01); *A61K 2800/95* (2013.01)

(58) Field of Classification Search
   None
   See application file for complete search history.

(56) References Cited

U.S. PATENT DOCUMENTS

| | | | |
|---|---|---|---|
| 2,782,790 A | 2/1957 | Hersh et al. | |
| 4,344,763 A | 8/1982 | Tolgyesi et al. | |
| 5,152,984 A | 10/1992 | Varaprath et al. | |
| 5,482,703 A | 1/1996 | Pings | |
| 6,106,820 A * | 8/2000 | Morrissey et al. | 424/78.18 |
| 6,953,572 B1 * | 10/2005 | Samain et al. | 424/70.12 |
| 6,953,584 B1 | 10/2005 | Samain et al. | |
| 6,986,886 B2 | 1/2006 | Hammond et al. | |
| 7,244,420 B1 | 7/2007 | Samain et al. | |
| 8,343,238 B1 | 1/2013 | Lopez et al. | |
| 8,506,651 B2 | 8/2013 | Lopez et al. | |
| 8,556,994 B2 | 10/2013 | Lopez et al. | |
| 8,591,872 B2 | 11/2013 | Singer et al. | |
| 2003/0003073 A1 | 1/2003 | Muller | |
| 2003/0095943 A1 | 5/2003 | Barbuzzi et al. | |
| 2003/0206933 A1 | 11/2003 | Schulze zur Wiesche et al. | |
| 2005/0129640 A1 | 6/2005 | Laurent | |
| 2007/0218028 A1 * | 9/2007 | Takai et al. | 424/70.12 |
| 2008/0226576 A1 | 9/2008 | Benabdillah et al. | |
| 2013/0213426 A1 | 8/2013 | Bui et al. | |
| 2014/0170105 A1 | 6/2014 | Chen et al. | |

FOREIGN PATENT DOCUMENTS

| | | | |
|---|---|---|---|
| EP | 0113418 | * | 7/1984 |
| EP | 0 159 628 A2 | | 10/1985 |
| EP | 1 532 967 A1 | | 5/2005 |
| EP | 1 767 189 A2 | | 3/2007 |
| EP | 1 935 398 A1 | | 6/2008 |
| FR | 2 783 164 A1 | | 3/2000 |
| FR | 2 783 165 A1 | | 3/2000 |
| FR | 2783167 A1 | | 3/2000 |
| FR | 2 798 063 A1 | | 3/2001 |
| FR | 2 891 142 A1 | | 3/2007 |
| FR | 2891141 A1 | | 3/2007 |
| FR | 2891143 A1 | | 3/2007 |
| FR | 2 910 276 A1 | | 6/2008 |
| WO | 89/04163 A1 | | 5/1989 |
| WO | 01/22931 A1 | | 4/2001 |

OTHER PUBLICATIONS

French Search Report for FR 0950604, dated Oct. 7, 2009.
English language abstract of EP 1 767 189 A2, Mar. 28, 2007.
English language abstract of FR 2 798 063 A1, Mar. 9, 2001.
English language abstract of FR 2 891 142 A1, Mar. 30, 2007.
English language abstract of FR 2 910 276 A1, Jun. 27, 2008.
Mckay, Amodimethicone and other Amine-functionalized Silicones, (/curlreading/curl-products/curlchemist-amodimethicone-and-other-amine-functionalized-silicones/), 2007, pp. 1-12.
Starch, Michael S., "Silicones in Hair Care Products," Drug and Cosmetic Industry, vol. 134, No. 6 (1984), pp. 38, 40, 42, 44, 102.
Larrey et al., "Hair Care: The Silicone Solution, Controlled Update of Silicone on Hair," Cosmetic News, Milan, IT, vol. 21, No. 118, (1998), pp. 40-44.
French Search Report for counterpart FR 0655758, dated Jul. 25, 2007.
Non-Final Office Action for copending U.S. Appl. No. 12/003,101, dated Oct. 1, 2009.
Final Office Action for copending U.S. Appl. No. 12/003,101, dated Nov. 22, 2010.
Non-Final Office Action for copending U.S. Appl. No. 12/003,101, dated Jul. 31, 2013.

(Continued)

*Primary Examiner* — Jennifer A Berrios
(74) *Attorney, Agent, or Firm* — The Marbury Law Group, PLLC

(57) ABSTRACT

The present application relates to a nondetergent cosmetic composition comprising at least one alkoxysilane comprising at least one basic functional group and at least one microbial gum. The present disclosure also relates to the use, for the treatment of keratin materials, such as the hair, for example, damaged, curly, dry or fine hair, of this composition, and also to a method of hair shaping comprising the application of said composition to the hair.

15 Claims, No Drawings

(56) References Cited

OTHER PUBLICATIONS

Final Office Action for copending U.S. Appl. No. 12/003,101, dated Mar. 24, 2014.
Non-Final Office Action for copending U.S. Appl. No. 12/003,101, dated Feb. 23, 2015.
Final Office Action for copending U.S. Appl. No. 12/003,101, dated Oct. 20, 2015.
Non-Final Office Action for copending U.S. Appl. No. 12/003,101, dated Dec. 27, 2016.
Final Office Action for copending U.S. Appl. No. 12/003,101, dated Sep. 25, 2017.

* cited by examiner

NONDETERGENT COSMETIC COMPOSITIONS COMPRISING AT LEAST ONE ALKOXYSILANE AND AT LEAST ONE MICROBIAL GUM AND STYLING USES

This application claims benefit of U.S. Provisional Application No. 61/154,861, filed Feb. 24, 2009. This application also claims benefit of priority under 35 U.S.C. § 119 to French Patent Application No. 0950604, filed Jan. 30, 2009.

The present disclosure relates to nondetergent cosmetic compositions comprising at least one cosmetically acceptable medium, at least one alkoxysilane comprising at least one basic functional group, and at least one microbial gum, and to the use thereof for shaping keratin fibers.

Hair treatment compositions containing alkoxysilanes are known in the art.

These compositions may, for example, make it possible to obtain styling effects on fine and curly hair. However, since these effects are not sufficiently strong and long-lasting, it is generally necessary to reapply the products after several days.

It has also been observed that, after several applications, i.e. several superimpositions of the compositions containing alkoxysilanes comprising solubilising functions, the hair may become dry, rough, and have the feel of damaged, sensitised hair.

It has been discovered that nondetergent cosmetic compositions comprising at least one cosmetically acceptable medium, at least one alkoxysilane comprising at least one basic functional group, and at least one microbial gum, may make it possible to solve these problems.

After applying the compositions disclosed herein to the hair, a satisfactory and long-lasting styling effect may be obtained. The hairstyle may exhibit body and volume. The hair may also be very easy to disentangle and very manageable and may be soft and smooth to the touch. These effects may further withstand several shampooings.

These beneficial effects may, for example, be visible on fine hair or on damaged or even very damaged hair, such as on bleached hair.

The compositions disclosed herein may also make it possible to obtain control of the hair shaping, such as control of the shape of the curls, on dry, curly hair.

Thus, at least one aspect of the present disclosure is a nondetergent cosmetic composition comprising at least one cosmetically acceptable medium, at least one alkoxysilane having at least one basic functional group, and at least one microbial gum.

Another aspect of the present disclosure is the use of a nondetergent cosmetic composition comprising at least one cosmetically acceptable medium, at least one alkoxysilane comprising at least one basic functional group, and at least one microbial gum, for the treatment of keratin materials, such as the hair, for example, for the treatment of damaged, curly, dry or fine hair.

Yet another aspect of the present disclosure is a method for shaping the hair, comprising applying the nondetergent cosmetic compositions disclosed herein to the hair.

Another aspect of the present disclosure relates to the use of the nondetergent cosmetic compositions for preventing the degradation of the feel of the hair that is generated by repeated applications of hair-shaping compositions comprising at least one alkoxysilane comprising at least one basic functional group.

As used herein, the term "nondetergent composition" is intended to mean that the composition comprises no more than 4% by weight of surfactants relative to the total weight of the composition.

The at least one alkoxysilane comprising at least one basic functional group that is present in the compositions disclosed herein, is chosen from organosilanes comprising one, two or three silicon atoms, such as one or two silicon atoms. They should also comprise at least one basic chemical function. The at least one basic chemical functional group may correspond to any function that confers a basic nature on the silicon compound, and is, for instance, an amine function such as a primary, secondary or tertiary amine function. The basic chemical function of the silicon compounds according to the present disclosure may optionally comprise other functions, such as, another amine function, an acid function or a halogen function.

The at least one alkoxysilane comprising at least one basic functional group that is present in the compositions according to the present disclosure, can also comprise at least two hydrolysable or hydroxyl groups per molecule. The hydrolysable groups are chosen, for example, from alkoxy, aryloxy and halogen groups. They may also optionally comprise other chemical functions such as acid functions.

According to at least one embodiment of the present disclosure, the at least one alkoxysilane comprising at least one basic functional group that is present in the compositions disclosed herein is chosen from the entities of formula (I):

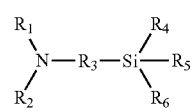

wherein:
$R_4$ is chosen from halogens, OR' and $R'_1$;
$R_5$ is chosen from halogens, OR" and $R'_2$;
$R_6$ is chosen from halogens, OR''' and $R'_3$;
$R_1$, $R_2$, $R_3$, R', R", R''', $R'_1$, $R'_2$ and $R'_3$ are each independently chosen from linear and branched, saturated and unsaturated hydrocarbon-based groups optionally bearing additional chemical groups such as acid or amine groups, it also being possible for $R_1$, $R_2$, R', R" and R''' to be hydrogens, and at least two of the $R_4$, $R_5$ and $R_6$ groups are different from the $R'_1$, $R'_2$ and $R'_3$ groups.

In at least one embodiment, the $R_1$, $R_2$, R', $R'_1$, $R'_2$, $R'_3$, R" and R''' groups are chosen from $C_1$-$C_{12}$ alkyl, $C_5$-$C_{14}$ aryl, ($C_1$-$C_8$)alkyl($C_5$-$C_{14}$)aryl and ($C_1$-$C_{14}$)aryl($C_1$-$C_8$) alkyl radicals.

In at least one embodiment, the $R_3$ group is chosen from $C_1$-$C_{12}$ alkylene, optionally substituted with an amino group, $C_5$-$C_{14}$ arylene, ($C_1$-$C_8$)alkylene($C_5$-$C_{14}$)arylene and ($C_5$-$C_{14}$)arylene($C_1$-$C_8$)alkylene radicals.

According to another embodiment of the present disclosure, the at least one alkoxysilane comprising at least one basic functional group corresponding to the formulae (I) is chosen from, for instance, 3-aminopropyltriethoxysilane, 3-aminopropylmethyldiethoxysilane, N-(2-aminoethyl)-3-aminopropylltriethoxysilane and 3-(2-aminoethylamino)propylmethyldiethoxysilane.

According to another embodiment, the at least one alkoxysilane comprising at least one basic functional group that is used according to the present disclosure is chosen from the entities of formula (II):

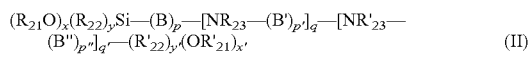

(II)

wherein:

$R_{21}$, $R_{22}$, $R'_{21}$ and $R'_{22}$ are each independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl and carbonyl groups, x is an integer ranging from 1 to 3, y=3-x, x' is an integer ranging from 1 to 3, y'=3-x', p=0 or 1, p'=0 or 1, p''=0 or 1, q=0 or 1, q'=0 or 1, it being understood that at least q or q' is other than zero, B, B' and B'' are each independently chosen from linear and branched $C_1$-$C_{20}$ alkylene divalent radicals, $R_{23}$ and $R'_{23}$ are each independently chosen from hydrogen atoms, and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_3$-$C_{20}$ alkyl ester, amine, amide, carboxyl, alkoxysilane, hydroxyl, carbonyl and acyl groups.

As explained above, $R_{21}$, $R_{22}$, $R'_{21}$, $R'_{22}$, $R_{23}$ and $R'_{23}$ are each independently chosen from hydrocarbon-based chains. As used herein, "hydrocarbon-based chain" is intended to mean a chain containing 1 to 30 carbon atoms, such as 1 to 10 carbon atoms.

In at least one embodiment, the aromatic ring contains from 6 to 30 carbon atoms, for example, an optionally substituted phenyl radical.

According to at least one embodiment, $R_{21}$=$R'_{21}$; $R_{22}$=$R'_{22}$; x=x'; y=y'; p=p'; B=B'; q=1 and q'=0.

In at least one embodiment, the at least one alkoxysilane comprising at least one basic functional group is chosen from the entities of formula (II), wherein:

$R_{21}$, $R_{22}$, $R'_{21}$ and $R'_{22}$, which may be identical or different, are chosen from $C_1$-$C_4$ alkyl groups, p=p'=1;

B and B', which may be identical or different, are chosen from linear $C_1$-$C_4$ alkylene groups, and $R_{23}$ is hydrogen.

For example, the at least one alkoxysilane comprising at least one basic functional group may comprise a substituent comprising a secondary amine function, such as the bis[3-(triethoxysilyl)propyl]amine of formula $(CH_3CH_2O)_3$—Si$(CH_2)_3NH(CH_2)_3Si(OCH_2CH_3)_3$ proposed by the company Fluorochem, the bis[trimethoxysilylpropyl]amine of formula $(CH_3O)_3$—Si$(CH_2)_3NH(CH_2)_3Si(OCH_3)_3$ proposed by the company Gelest, the bis[methyldiethoxysilylpropyl]amine of formula $(CH_3CH_2O)_2CH_3Si(CH_2)_3NH(CH_2)_3SiCH_3(OCH_2CH_3)_2$ proposed by the company Gelest and the bis[3-trimethoxysilylpropyl]ethylenediamine of formula $(CH_3O)_3Si(CH_2)_3NH(CH_2)_2NH(CH_2)_3Si(OCH_3)_3$ proposed by the company Gelest. In at least one embodiment of the present disclosure, bis[3-(triethoxysilyl)propyl]amine and bis[methyldiethoxysilylpropyl]amine are used.

According to another embodiment of the present disclosure, the at least one alkoxysilane comprising at least one basic functional group is chosen from the entities of formula (III):

(III)

wherein:

$R_{24}$ and $R_{25}$ are each independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl and carbonyl groups, x''=2 or 3;

y''=3-x'';

n'=0 or 1; and n''=0 or 1;

E and E' are each independently chosen from linear and branched $C_1$-$C_{20}$ alkylene divalent radicals, $R_{26}$ and $R_{27}$ are each independently chosen from a hydrogen atom and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups, r is an integer ranging from 0 to 4, r'=0 or 1, and each instance of $R_{28}$ is independently chosen from a hydrogen atom and linear and branched, saturated and unsaturated, $C_1$-$C_{10}$, hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups.

As explained above, $R_{24}$, $R_{25}'$ $R_{26}$ and $R_{27}$ are each independently chosen from hydrocarbon-based chains. As used herein, "hydrocarbon-based chain" is intended to mean a chain containing from 1 to 30 carbon atoms, such as containing from 1 to 10 carbon atoms.

In at least one embodiment, the aromatic ring contains from 6 to 30 carbon atoms, for example an optionally substituted phenyl radical.

The at least one alkoxysilane comprising at least one basic functional group of formula (III), may be chosen wherein:

$R_{24}$ is a $C_1$-$C_4$ alkyl, x''=3, n'=n''=1; r=r'=0, and $R_{26}$ and $R_{27}$ are each independently chosen from a hydrogen atom and groups chosen from $C_1$-$C_4$ alkyl, $C_1$-$C_4$ hydroxyalkyl and $C_1$-$C_4$ aminoalkyl groups.

In at least one embodiment, the at least one alkoxysilane comprising at least one basic functional group of formula (III), may be chosen from, for example:

3-(m-aminophenoxy)propyltrimethoxysilane, of formula:

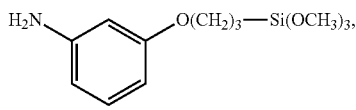

p-aminophenyltrimethoxysilane, of formula:

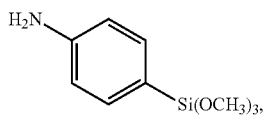

and
N-(2-aminoethylaminomethyl)phenethyltrimethoxysilane, of formula:

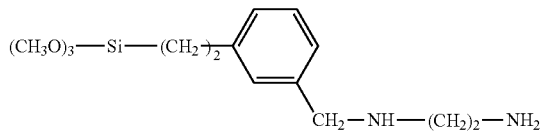

In another embodiment, the at least one alkoxysilane comprising at least one basic functional group may comprise at least one primary or secondary amine function.

In yet another embodiment, the at least one alkoxysilane comprising at least one basic functional group that can be used in the compositions disclosed herein, correspond to formula (I):

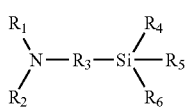

wherein:
$R_1$ and $R_2$, are each independently chosen from a hydrogen atom and ethyl, propyl and aminoethyl groups;
$R_3$ is chosen from ethyl, propyl and methylphenethyl groups;
$R_4$, $R_5$ and $R_6$ are each independently chosen from methyl, methoxy and ethoxy groups.

Non-limiting examples of the at least one alkoxysilane of formula (I) include, but are not limited to: 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and N-(2-aminoethylaminomethyl)phenethyltrimethoxysilane of formula:

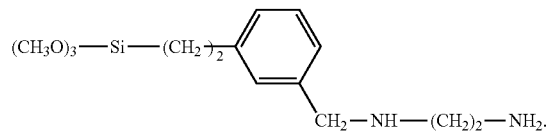

The at least one alkoxysilane comprising at least one basic functional group is present in a total amount ranging from 0.1% to 20%, such as ranging from 1% to 15% by weight of the total weight of the composition.

As disclosed herein, the term "microbial gums" is intended to mean substances synthesised by sugar fermentation by microorganisms. The at least one microbial gum, according to the present disclosure, may also be chosen from sclerotium gums, gellan gums, pullulan gums, curdlan gums, xanthan gums, grifolan gums, lentinan gums, schizophyllan gums, spirulinan gums and krestin gums;

Suitable examples of the at least one microbial gum include, but are not limited to the sclerotium gums produced by *Sclerotium rolfsii*, the gellan gums produced by *Pseudomonas elodea* or *Sphingomonias*, the pullulan gums produced by *Aureobacidium pullulens*, the curdlan gums produced by *Alcaligenes* of *Faecalis myxogenes* type, the xanthan gums produced by numerous organisms, including *Leuconostoc mesenteroides* and *Leuconostoc dextrantum*, the grifolan gums produced by *Grifola frondara*, the lentinan gums produced by *Lentinus edodes*, the schizophyllan gums produced by *Schizophyllum commine*, the spirulinan gums produced by *Spirulina sybsyla* and the krestin gums produced by *Coriates versicolor*.

Non-limiting mention may also be made of the xanthan gums produced by the bacterium *Xanthomonas campestri* and the mutants and variants thereof. These xanthan gums generally have a molecular weight ranging from 1,000,000 to 50,000,000.

In at least one embodiment of the present disclosure, xanthan and sclerotium gums are used, for example, sclerotium gums.

The at least one microbial gum may be present in the composition in a total amount ranging from 0.01% to 10%, such as ranging from 0.1% to 4%, by weight, of the total weight of the composition.

In at least one embodiment, the weight ratio between the at least one microbial gum and the at least one alkoxysilane comprising at least one basic functional group ranges from 1/20 to 1/3.

The compositions according to the present disclosure may also comprise at least one additional thickener different from the at least one microbial gum, for instance carboxyvinyl polymers and copolymers, (alkyl)acrylic polymers and copolymers, (alkyl)acrylamide polymers and copolymers, poly(oxyalkylene) glycols, poly(oxyalkylene) glycol esters, cellulose derivatives, alginates, starch derivatives, natural gums such as guar or carob gums, derivatives of chitin and of chitosan, carrageenans, clays, and mixtures thereof.

The cellulose derivatives are, for example, hydroxyalkylcelluloses, such as hydroxyethylcelluloses, hydroxypropylcelluloses, and hydroxypropylmethylcelluloses.

The at least one additional thickening polymer may, for instance, comprise at least one fatty chain. Non-limiting mention may thus be made of cetyl hydroxyethylcelluloses.

The at least one additional thickener may be present in a total amount ranging from 0.05% to 15%, such as ranging from 0.5% to 10% by weight of the composition.

The cosmetic composition according to the present disclosure may also comprise at least one organic solvent, for instance, in a total amount ranging from 0.05% to 40%, for example, ranging from 1% to 20% by weight, relative to the total weight of the composition.

This organic solvent may be chosen from, for example, $C_2$ to $C_4$ lower alcohols, such as ethanol, and polyols such as propylene glycol or glycerol, and polyol ethers.

In at least one embodiment, the cosmetically acceptable medium is aqueous or aqueous-alcoholic.

The compositions according to the present disclosure may also contain other cosmetically acceptable adjuvants, such as surfactants, co-thickeners, penetrating agents, fragrances, dyes, plasticizers, buffers, and various customary adjuvants such as waxes, cyclic or linear or branched, volatile or non-volatile silicones which are optionally organomodified, for example, with amine groups, and are different from the at least one alkoxysilane comprising basic functional group at least one basic functional group basic functional group disclosed herein, ceramides, pseudoceramides, plant, mineral or synthetic oils, vitamins or provitamins such as panthenol, opacifiers, reducing agents, emulsifiers, preservatives, inorganic fillers, pearlescent agents, glitter flakes, sunscreens, proteins, anionic, nonionic, cationic or amphoteric fixing polymers, hydrating agents, emollients, demulcents, antifoams, antiperspirants, free-radical scavengers, bactericides, sequestering agents, antidandruff agents, antioxidants, basifying agents, acids, fragrances and any other additive conventionally used in cosmetic compositions intended to be applied to the hair.

The surfactants that can be used in accordance with the present disclosure include, anionic, nonionic, amphoteric, cationic surfactants, and mixtures thereof.

Suitable examples of anionic surfactants that can be used, include, but are not limited to salts, such as alkali metal salts, for instance, sodium salts, ammonium salts, amine salts, aminoalcohol salts or alkaline earth metal salts, for example magnesium salts, of the following compounds: alkyl sulphates, alkyl ether sulphates, alkylamido ether sulphates, alkylaryl polyether sulphates, monoglyceride sulphates; alkylsulphonates, alkylamidesulphonates, alkylarylsulphonates, α-olefin sulphonates, paraffin sulphonates; alkyl sulphosuccinates, alkyl ether sulphosuccinates, alkylamide sulphosuccinates; alkyl sulphoacetates; acylsarcosinates; and acylglutamates, the alkyl and acyl groups of all these compounds containing from 6 to 24 carbon atoms and the aryl group chosen from phenyl and benzyl groups, and mixtures thereof.

Other examples of anionic surfactants that may be used include, but are not limited to $C_6$-$C_{24}$ alkyl esters of polyglycosidecarboxylic acids, such as alkyl glucosidecitrates, alkyl polyglycosidetartrates, and alkyl polyglycosidesulphosuccinates; alkyl sulphosuccinamates, acylisethionates and N-acyltaurates, the alkyl or acyl group of all these compounds containing from 12 to 20 carbon atoms, acyl lactylates, wherein the acyl group comprises from 8 to 20 carbon atoms.

In addition, non-limiting mention may also be made of alkyl-D-galactosideuronic acids and salts thereof, and also polyoxyalkylenated ($C_6$-$C_{24}$)alkyl ether carboxylic acids, polyoxyalkylenated ($C_6$-$C_{24}$)alkyl($C_6$-$C_{24}$)aryl ether carboxylic acids, polyoxyalkylenated ($C_6$-$C_{24}$)alkylamido ether carboxylic acids and salts thereof, such as those comprising from 2 to 50 ethylene oxide groups, and mixtures thereof.

Suitable examples of nonionic surfactants that can be used according to the present disclosure include, but are not limited to compounds that are disclosed, for example in "Handbook of Surfactants" by M. R. Porter, publishers Blackie & Son (Glasgow and London), 1991, pp 116-178). Non-limiting examples, include, but are not limited to alcohols, alpha-diols, ($C_1$-$C_{20}$)alkylphenols or fatty acids that are polyethoxylated, polypropoxylated or polyglycerolated, having a fatty chain containing, for example, from 8 to 18 carbon atoms, it being possible for the number of ethylene oxide or propylene oxide groups to range, for example from 2 to 50 and it being possible for the number of glycerol groups to range, for example from 2 to 30.

Non-limiting mention may also be made of copolymers of ethylene oxide and of propylene oxide, condensates of ethylene oxide and of propylene oxide with fatty alcohols; polyethoxylated fatty amides having, for instance, from 2 to 30 mol of ethylene oxide; polyglycerolated fatty amides comprising on average 1 to 5 glycerol groups, such as 1.5 to 4 glycerol groups; ethoxylated fatty acid esters of sorbitan having from 2 to 30 mol of ethylene oxide; fatty acid esters of sucrose, fatty acid esters of polyethylene glycol, ($C_6$-$C_{24}$ alkyl)polyglucosides, N—($C_6$-$C_{24}$ alkyl)glucamine derivatives, amine oxides, such as ($C_{10}$-$C_{14}$ alkyl)amine oxides or N—($C_{10}$-$C_{14}$ acyl)aminopropylmorpholine oxides; and mixtures thereof.

Suitable examples of amphoteric surfactants that can be used in the compositions according to the present disclosure, include, but are not limited to derivatives of secondary or tertiary aliphatic amines, wherein the aliphatic group is a linear or branched chain comprising 8 to 22 carbon atoms and containing at least one water-solubilising anionic group, such as, for example, a carboxylate, sulphonate, sulphate, phosphate or phosphonate group; mention may also be made of ($C_8$-$C_{20}$)alkyl betaines, sulphobetaines, ($C_8$-$C_{20}$)alkylamido($C_6$-$C_8$)alkyl betaines or ($C_8$-$C_{20}$)alkylamido($C_6$-$C_8$) alkyl sulphobetaines; and mixtures thereof.

Among the amine derivatives, non-limiting mention may be made, for example, of the products sold under the name MIRANOL®, as described in U.S. Pat. No. 2,528,378 and U.S. Pat. No. 2,781,354 and classified in the CTFA dictionary, 3rd edition, 1982, under the names Amphocarboxyglycinate and Amphocarboxypropionate, with the respective structures (1) and (2):

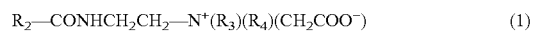

$$R_2-CONHCH_2CH_2-N^+(R_3)(R_4)(CH_2COO^-) \quad (1)$$

wherein:

$R_2$ is chosen from alkyl groups derived from an acid $R_2$—COOH present in hydrolysed coconut oil, and heptyl, nonyl and undecyl groups, $R_3$ is a beta-hydroxyethyl group, and $R_4$ is a carboxymethyl group;

and

$$R_2-CONHCH_2CH_2-N(B)(C) \quad (2)$$

wherein:

B is —$CH_2CH_2OX'$,

C is —$(CH_2)_z$—Y', with z=1 or 2,

X' is chosen from —$CH_2CH_2$—COOH and a hydrogen atom,

Y' is chosen from —COOH and —$CH_2$—CHOH—$SO_3H$, and $R_2$ is chosen from alkyl groups of an acid $R_2$—COOH present in hydrolysed linseed oil or coconut oil, an alkyl group, such as a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of non-limiting example, mention may be made of the cocoamphodiacetate sold under the trade name MIRANOL® C2M concentrated by the company Rhodia.

In at least one embodiment, amphoteric surfactants chosen from ($C_8$-$C_{20}$)alkyl betaines, such as cocobetaine, ($C_8$-$C_{20}$)alkylamido($C_6$-$C_8$) alkyl betaines, such as cocamidobetaine, alkylamphodiacetates such as disodium cocoamphodiacetate, and mixtures thereof, are used.

The composition according to the present disclosure may also comprise at least one cationic surfactant, such as the salts of optionally polyoxyalkylenated primary, secondary or tertiary fatty amines, quaternary ammonium salts, such as tetraalkylammonium, alkylamidoalkyltrialkylammonium, trialkylbenzylammonium, trialkylhydroxyalkylammonium or alkylpyridinium chlorides or bromides, imidazoline derivatives; or amine oxides of cationic nature.

The anionic, nonionic, amphoteric and cationic surfactants described above may be used alone or as mixtures, and is present in the compositions disclosed herein in an amount less than 4%, such as ranging from 0.01% to 4% by weight, for instance, ranging from 0.1% to 2% by weight, relative to the total weight of the composition.

In at least one embodiment, the composition according to the present disclosure further comprises at least one fixing polymer and/or at least one silicone and/or at least one fatty substance.

Non-limiting examples of suitable silicones include, but are not limited to cyclic, linear and branched, volatile and non-volatile silicones which are optionally modified with organic groups and which have a viscosity of $5 \times 10^{-6}$ to 2.5 m$^2$/s at 25° C., such as a viscosity of $1 \times 10^{-5}$ to 1 m$^2$/s.

The silicones that can be used in accordance with the present disclosure may be soluble or insoluble in the composition, for example may be polyorganosiloxanes that are insoluble in the compositions disclosed herein. They may be, for example, in the form of oils, waxes, resins or gums. These silicones are different from the at least one alkoxysilane comprising at least one basic functional group that are used in the present disclosure.

The organopolysiloxanes are defined in greater detail in the book by Walter Noll "Chemistry and Technology of Silicones" (1968), Academie Press. They may be volatile or non-volatile.

When they are volatile, the silicones are, for example, chosen from silicones having a boiling point ranging from 60° C. to 260° C., such as:

(i) cyclic silicones comprising from 3 to 7, such as from 4 to 5 silicon atoms. These are, for example, octamethylcyclotetrasiloxane sold under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Non-limiting mention may also be made of cyclocopolymers of the dimethylsiloxane/methylalkylsiloxane type, such as SILICONE VOLATILE® FZ 3109 sold by the company Union Carbide, of formula:

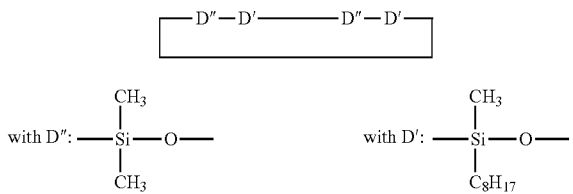

Mention may also be made in a non-limiting manner, of mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m$^2$/s at 25° C. An non-limiting example is decamethyltetrasiloxane sold, for instance, under the name SH 200 by the company Toray Silicone. Silicones belonging to this category are, for example, also described in the article published in *Cosmetics and Toiletries*, Vol. 91, January 76, pp. 27-32, Todd & Byers "Volatile Silicone Fluids for Cosmetics".

Non-volatile silicones, such as polyalkylsiloxanes, polyarylsiloxanes, polyalkylarylsiloxanes, silicone gums and resins, polyorganosiloxanes modified with organofunctional groups, and mixtures thereof, may be used in at least one embodiment of the present disclosure.

These silicones are, for example, chosen from polyalkylsiloxanes, among which mention may be made mainly of polydimethylsiloxanes containing trimethylsilyl end groups. The viscosity of the silicones is measured at 25° C. according to ASTM 445 standard Appendix C.

Among these polyalkylsiloxanes, mention may be made, in a non-limiting manner, of the following commercial products:

the SILBIONE® oils of the 47 and 70 047 series or the MIRASIL® oils sold by Rhodia, such as, for example, the oil 70 047 V 500 000;

the oils of the MIRASIL® series sold by the company Rhodia;

the oils of the 200 series from the company Dow Corning, such as DC200 with a viscosity of 60 000 mm$^2$/s;

the VISCASIL® oils from General Electric and certain oils of the SF series (SF 96, SF 18) from General Electric.

Non-limiting mention may also be made of polymethylsiloxanes containing dimethylsilanol end groups, known by the name dimethiconol (CTFA), such as the oils of the 48 series from the company Rhodia.

In this category of polyalkylsiloxanes, non-limiting mention may also be made of the products sold under the names ABIL WAX® 9800 and 9801 by the company Goldschmidt, which are poly(C$_1$-C$_{20}$)alkylsiloxanes.

The polyalkylarylsiloxanes are chosen, for instance, from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Suitable examples of polyalkylarylsiloxanes, include, but are not limited to the products sold under the following names:

the SILBIONE® oils of the 70 641 series from Rhodia;

the oils of the RHODORSIL® 70 633 and 763 series from Rhodia;

the oil DOW CORNING 556 Cosmetic Grade Fluid from Dow Corning;

the silicones of the PK series from Bayer, such as the product PK20;

the silicones of the PN and PH series from Bayer, such as the products PN1000 and PH1000; and certain oils of the SF series from General Electric, such as SF 1023, SF 1154, SF 1250 and SF 1265.

The silicone gums that can be used in accordance with the present disclosure are, for instance, polyorganosiloxanes having high number-average molecular weights ranging from 200,000 to 1,000,000, used alone or as mixtures in a solvent. These solvents can be chosen, for instance, from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Non-limiting mention may be made, for instance, of the following products:
- polydimethylsiloxane gums,
- polydimethylsiloxane/methylvinylsiloxane gums,
- polydimethylsiloxane/diphenylsiloxane gums,
- polydimethylsiloxane/phenylmethylsiloxane gums, and
- polydimethylsiloxane/diphenylsiloxane/methylvinylsiloxane gums.

Products that can be used in accordance with the present disclosure, include, but are not limited to:

mixtures formed from a polydimethylsiloxane hydroxylated at the end of the chain, or dimethiconol (CTFA) and from a cyclic polydimethylsiloxane also called cyclomethicone (CTFA), such as the product Q2 1401 sold by the company Dow Corning;

mixtures of a polydimethylsiloxane gum and a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane;

mixtures of two PDMSs of different viscosities, such as a mixture of a PDMS gum and a PDMS oil, such as the product SF 1236 from the company General Electric. The product SF 1236 is the mixture of an SE 30 gum defined above, having a viscosity of 20 m$^2$/s, and an SF 96 oil, with a viscosity of 5×10$^{-6}$ m$^2$/s. This product contains, for instance, 15% SE 30 gum and 85% SF 96 oil.

The organopolysiloxane resins that can be used in accordance with the present disclosure are crosslinked siloxane systems containing the following units:

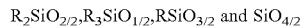

$R_2SiO_{2/2}, R_3SiO_{1/2}, RSiO_{3/2}$ and $SiO_{4/2}$ wherein R is chosen from hydrocarbon-based groups comprising 1 to 16 carbon atoms and a phenyl group. In at least one embodiment of the present disclosure, R is chosen from $C_1$-$C_4$ lower alkyl groups, such as methyl, and phenyl groups.

Among these resins, non-limiting mention may be made of the product sold under the name DOW CORNING 593 or those sold under the names SILICONE FLUID SS 4230 and SS 4267 by the company General Electric, which are silicones of dimethyl/trimethylsiloxane structure.

Mention may also be made, in a non-limiting manner, of the trimethylsiloxysilicate type resins sold, for example, under the names X22-4914, X21-5034 and X21-5037 by the company Shin-Etsu.

The organomodified silicones that can be used in accordance with the present disclosure are silicones as defined above and containing in their structure at least one organofunctional groups attached via a hydrocarbon-based group.

Among the organomodified silicones, non-limiting mention may be made of polyorganosiloxanes comprising:

polyethyleneoxy and/or polypropyleneoxy groups optionally containing $C_6$-$C_{24}$ alkyl groups, such as the products known as dimethicone copolyol sold by the company Dow Corning under the name DC 1248 or the oils SILWET® L 722, L 7500, L 77, L 711 from the company Union Carbide and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and DOW CORNING 929 or 939 or DOW CORNING 2-8299 by the company Dow Corning or the product sold under the name BELSIL ADM LOG 1 by the company Wacker. The substituted amine groups are, for instance, $C_1$-$C_4$ aminoalkyl groups;

thiol groups such as the products sold under the names GP 72A and GP 71 from Genesee;

alkoxylated groups such as the product sold under the name SILICONE COPOLYMER F-755 by SWS Silicones and ABIL WAX® 2428, 2434 and 2440 by the company Goldschmidt;

hydroxylated groups such as the polyorganosiloxanes containing a hydroxyalkyl functional group;

alkoxyalkyl groups such as the polyorganosiloxanes described in U.S. Pat. No. 4,957,732;

anionic groups of carboxylic type, such as the products described in European Patent No. 0 186 507 from the company Chisso Corporation, or of alkylcarboxylic type, such as those present in the product X-22-3701 E from the company Shin-Etsu; 2-hydroxyalkyl sulphonate; 2-hydroxyalkyl thiosulphate such as the products sold by the company Goldschmidt under the names ABE® S201 and ABIL® S255;

hydroxyacrylamino groups, such as the polyorganosiloxanes described in European Patent Application No. 0 EP 342 834. Mention may be made, for example, of the product Q2-8413 from the company Dow Corning.

The silicones described above may be used, alone or as a mixture, in an amount ranging from 0.01% to 20% by weight, such as ranging from 0.1% to 5% by weight.

The compositions of the present disclosure may also comprise fatty substances such as mineral, plant, animal and synthetic oils, waxes, fatty esters, ethoxylated or non-ethoxylated fatty alcohols, and fatty acids.

Suitable oils that can be used in the compositions of the present disclosure, include, but are not limited to:

hydrocarbon-based oils of animal origin, such as perhydrosqualene;

hydrocarbon-based oils of plant origin, such as liquid fatty acid triglycerides containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, such as volatile or non-volatile liquid paraffins, and derivatives thereof, petroleum jelly, polydecenes, hydrogenated polyisobutene such as PARLEAM®; isoparaffins, for instance, isohexadecane and isodecane;

partially hydrocarbon-based and/or silicone-based fluoro oils, for instance those described in Japanese Patent No. JP-A-2-295 912; fluoro oils that may also be mentioned include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The waxes that are suitable for the compositions disclosed herein, include but are not limited to carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that can be used according to the present disclosure are, for instance, marine waxes such as the product sold by the company Sophim under the reference M82, and polyethylene waxes and polyolefin waxes.

The saturated or unsaturated fatty acids are, for instance, chosen from myristic acid, palmitic acid, stearic acid, behenic acid, oleic acid, linoleic acid, linolenic acid and isostearic acid.

The fatty esters are for example, chosen from carboxylic acid esters, such as mono-, di-, tri-, and tetracarboxylic esters.

The carboxylic acid esters are, in at least one embodiment, chosen from saturated and unsaturated, linear and branched $C_1$-$C_{26}$ aliphatic acids and saturated and unsaturated, linear and branched $C_1$-$C_{26}$ aliphatic alcohols, the total carbon number of the esters being greater than or equal to 10.

Among the suitable monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, and 2-hexyldecyl laurate.

Also useful herein are esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

Non-limiting mention may also be made of diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate and neopentyl glycol diheptanoate.

In at least one embodiment of the present disclosure, the esters may be chosen from ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate.

As fatty alcohols, non-limiting mention may be made of linear or branched, saturated or unsaturated fatty alcohols comprising from 8 to 26 carbon atoms, such as cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The fatty substances are present in an amount ranging from 0.1% to 50%, such as ranging from 1% to 30%, for example, ranging from 2% to 20% by weight of the total composition.

As used herein, the term "fixing polymer" is intended to mean any polymer that makes it possible to give a shape to a head of hair or to hold a head of hair in a given shape.

All known anionic, cationic, amphoteric and nonionic fixing polymers and mixtures thereof in the art may be used in the compositions according to the present disclosure.

The fixing polymers may be soluble in the cosmetically acceptable medium or insoluble in this same medium and used, in this case, in the form of dispersions of solid or liquid particles of polymer (latex or pseudolatex).

The anionic fixing polymers used may be, for example, polymers comprising groups derived from carboxylic, sulphonic or phosphoric acid and have a number-average molecular weight ranging from 500 to 5,000,000.

The carboxylic groups are derived from unsaturated monocarboxylic and dicarboxylic acid monomers such as those corresponding to the formula:

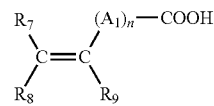

wherein n is an integer ranging from 0 to 10, $A_1$ is a methylene group, optionally connected to the carbon atom of the unsaturated group or to the neighboring methylene group when n is greater than 1, via a heteroatom such as oxygen or sulphur, $R_7$ is chosen from a hydrogen atom, and phenyl and benzyl groups, $R_8$ is chosen from a hydrogen atom, lower alkyl groups and carboxyl groups; and $R_9$ is chosen from a hydrogen atom, lower alkyl groups, —$CH_2$—COOH, phenyl groups and benzyl groups.

In the abovementioned formula, a lower alkyl group is understood to mean a group having 1 to 4 carbon atoms, for example, methyl and ethyl groups.

Non-limiting examples of anionic fixing polymers comprising carboxylic groups that may be used according to the present disclosure are:

A) Copolymers of acrylic acid or methacrylic acid or salts thereof and of acrylamide, sold in the form of the sodium salts thereof under the names RETEN 421, 423 or 425 by the company Hercules, B) Copolymers of acrylic acid or methacrylic acid with a monoethylenic monomer such as ethylene, styrene, vinyl esters, acrylic or methacrylic acid esters, optionally grafted onto a polyalkylene glycol such as polyethylene glycol, and optionally crosslinked. Such polymers are described for example in French Patent No. 1 222 944 and German Patent Application No. 2 330 956, the copolymers of this type comprising an optionally N-alkylated and/or hydroxyalkylated acrylamide unit in their chain, as described for instance in Luxembourg Patent Application Nos. 75370 and 75371 or proposed under the name QUADRAMER by the company American Cyanamid. Mention may also be made, in a non-limiting manner, of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as the product sold by the company ISP under the name ACRYLIDONE® LM, and methacrylic acid/ethyl acrylate/tert-butyl acrylate terpolymers such as the product sold under the name LUVIMER® 100 P by the company BASF.

Non-limiting mention may also be made of methacrylic acid/acrylic acid/ethyl acrylate/methyl methacrylate copolymers as an aqueous dispersion, sold under the name AMERHOLD® DR 25 by the company Amerchol;

C) Crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon chain such as those comprising at least 5 carbon atoms, it being possible for these polymers optionally to be grafted or crosslinked, or alternatively another vinyl, allyl or methallyl ester monomer of an α- or β-cyclic carboxylic acid. Such polymers are described, for example, in French Patent Nos. 1 222 944, 1 580 545, 2 265 782, 2 265 781, 1 564 110 and 2 439 798. Examples of commercial products falling into this class include, but are not limited to the resins 28-29-30, 26-13-14 and 28-13-10 sold by the company National Starch.

D) Copolymers of $C_4$-$C_8$ monounsaturated carboxylic acids or anhydrides chosen from:

copolymers comprising (i) at least one maleic, fumaric or itaconic acids or anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described, for instance, in U.S. Pat. Nos. 2,047,398, 2,723,248 and 2,102,113 and GB Patent No. 839 805. Commercial products are, for instance, those sold under the names GANTREZ® AN or ES by the company ISP, copolymers comprising (i) at least one maleic, citraconic or itaconic anhydride units and (ii) at least one monomers chosen from allyl or methallyl esters optionally comprising at least one acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in French Patent Nos. 2 350 384 and 2 357 241.

E) Polyacrylamides comprising carboxylate groups.

Homopolymers and copolymers comprising sulphonic groups are polymers comprising vinylsulphonic, styrenesulphonic, naphthalenesulphonic or acrylamido-alkylsulphonic units.

These polymers may be chosen, for instance, from:

polyvinylsulphonic acid salts having a molecular weight ranging from 1000 to 100,000, and also the copolymers with an unsaturated comonomer such as acrylic acid or methacrylic acid and esters thereof, and also acrylamide or derivatives thereof, vinyl ethers and vinylpyrrolidone;

polystyrenesulphonic acid salts such as the sodium salts sold, for example, under the name FLEXAN® 500 and FLEXAN® 130 by National Starch. These compounds are described, for example in French Patent No. FR 2 198 719;

polyacrylamidesulphonic acid salts such as those mentioned in U.S. Pat. No. 4,128,631, for example the poly-acrylamidoethylpropanesulphonic acid sold under the name COSMEDIA POLYMER HSP 1180 by Henkel.

Another non-limiting example of an anionic fixing polymer that can be used according to the present disclosure, includes the branched block anionic polymer sold under the name FIXATE G-100 by the company Noveon.

According to at least one embodiment of the present disclosure, the anionic fixing polymers are chosen from acrylic acid copolymers such as the acrylic acid/ethyl acrylate/N-tert-butylacrylamide terpolymers sold, for instance, under the name ULTRAHOLD® Strong by the company BASF, crotonic acid-derived copolymers such as the vinyl acetate/vinyl tert-butylbenzoate/crotonic acid terpolymers and the crotonic acid/vinyl acetate/vinyl neododecanoate terpolymers sold, for instance, under the name RESINE 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name GANTREZ® by the company ISP, the methacrylic acid/methyl methacrylate copolymers sold under the name EUDRAGIT® L by the company Rohm Pharma, the methacrylic acid/ethyl acrylate copolymers sold under the name LUVIMER® Maex or MAE by the company BASF, the vinyl acetate/crotonic acid copolymers sold under the name LUVISET CA 66 by the company BASF, the vinyl acetate/crotonic acid copolymers grafted with polyethylene glycol, sold under the name ARISTOFLEX® A by the company BASF, and the polymer sold under the name FIXATE G-100 by the company Noveon.

Among the anionic fixing polymers mentioned above, non-limiting mention may be made, for example, of the monoesterified methyl vinyl ether/maleic anhydride copolymers sold under the name GANTREZ® ES 425 by the company ISP, the acrylic acid/ethyl acrylate/N-tert-butylacrylamide terpolymers sold under the name ULTRAHOLD® Strong by the company BASF, the copolymers of methacrylic acid and of methyl methacrylate sold under the name EUDRAGIT® L by the company Rohm Pharma, the vinyl acetate/vinyl tert-butylbenzoate/crotonic acid terpolymers and the crotonic acid/vinyl acetate/vinyl neododecanoate terpolymers sold under the name RESINE 28-29-30 by the company National Starch, the copolymers of methacrylic acid and of ethyl acrylate sold under the name LUVIMER® MAEX or MAE by the company BASF, the vinylpyrrolidone/acrylic acid/lauryl methacrylate terpolymers sold under the name ACRYLIDONE® LM by the company ISP, and the polymer sold under the name FIXATE G-100 by the company Noveon.

The cationic fixing film-forming polymers that can be used according to the present disclosure are chosen, for instance, from polymers comprising primary, secondary, tertiary and/or quaternary amine groups forming part of the polymer chain or directly attached thereto, and having a molecular weight ranging from 500 to about 5,000,000, such as ranging from 1000 to 3,000,000.

Among these polymers, non-limiting mention may be made for instance of the following cationic polymers:

(1) homopolymers or copolymers derived from acrylic or methacrylic esters or amides and comprising at least one of the units of the following formulae:

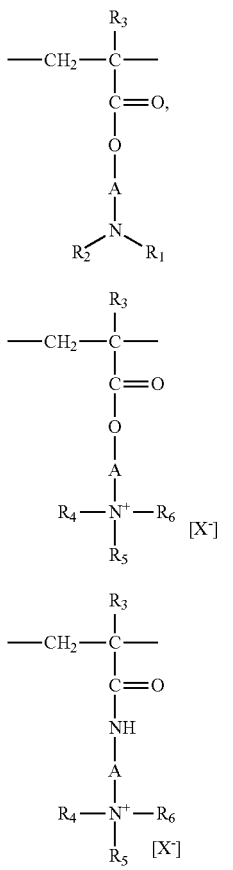

(A)

(B)

(C)

wherein:

R$_3$ is chosen from a hydrogen atom and a CH$_3$ radical;

A is chosen from linear and branched alkyl groups comprising 1 to 6 carbon atoms and hydroxyalkyl groups comprising 1 to 4 carbon atoms;

R$_4$, R$_5$ and R$_6$, which may be identical or different, are each independently chosen from alkyl groups having from 1 to 18 carbon atoms and benzyl radicals;

R$_1$ and R$_2$, which may be identical or different, are each independently chosen from a hydrogen atom and alkyl groups having from 1 to 6 carbon atoms;

X is a methosulphate anion or a halide such as chloride or bromide.

The copolymers of the family (1) also contain at least one unit derived from comonomers that may be chosen from the family of acrylamides, methacrylamides, diacetone acrylamides, acrylamides and methacrylamides substituted on the nitrogen with lower (C$_{1-4}$) alkyl groups, groups derived from acrylic or methacrylic acids or esters thereof, vinyllactams such as vinylpyrrolidone or vinylcaprolactam, and vinyl esters.

Thus, among these copolymers of the family (1), non-limiting mention may be made of:

copolymers of acrylamide and of dimethylaminoethyl methacrylate quaternized with dimethyl sulphate or with a dimethyl halide, such as the product sold under the name HERCOFLOC® by the company Hercules, copolymers of acrylamide and of methacryloyloxyethyl-trimethylammonium chloride, described, for example, in European Patent Application No. EP-A-080 976 and sold under the name BINA QUAT P 100 by the company Ciba Geigy, the copolymer of acrylamide and of methacryloyloxyeth-yltrimethylammonium methosulphate, such as the product sold under the name RETEN by the company Hercules, quaternized or non-quaternized vinylpyrrolidone/dialkylaminoalkyl acrylate or methacrylate copolymers, such as the products sold under the name "GAFQUAT®" by the company ISP, such as, for example, "GAFQUAT® 734" or "GAFQUATt® 755", or alternatively the products known as "COPOLYMER® 845, 958 and 937". These polymers are described, for example, in detail in French Patent Nos. 2 077 143 and 2 393 573, fatty-chain polymers containing a vinylpyrrolidone unit, such as the products sold under the name STYLEZE W20 and STYLEZE W10 by the company ISP, dimethylaminoethyl methacrylate/vinylcaprolactam/vinyl-pyrrolidone terpolymers, such as the product sold under the name GAFFIX VC 713 by the company ISP, and quaternized vinylpyrrolidone/dimethylaminopropyl methacrylamide copolymers, such as the products sold under the name "GAFQUAT® HS100" by the company ISP;

(2) cationic guar gums, for example cationic guar gums comprising a quaternary ammonium, such as those described in U.S. Pat. Nos. 3,589,578 and 4,031,307, such as guar gums containing trialkylammonium cationic groups. Such products are sold for example under the trade names JAGUAR C13S, JAGUAR C 15 and JAGUAR C 17 by the company Meyhall;

(3) quaternary copolymers of vinylpyrrolidone and of vinylimidazole;

(4) chitosans or salts thereof; the salts that can be used are, for instance, chitosan acetate, lactate, glutamate, gluconate or pyrrolidonecarboxylate.

Among these compounds, non-limiting mention may be made of chitosan having a degree of deacetylation of 90.5% by weight, sold under the name KYTAN BRUT Standard by the company Aber Technologies, and chitosan pyrrolidonecarboxylate sold under the name KYTAMER® PC by the company Amerchol;

(5) cationic cellulose derivatives such as copolymers of cellulose or of cellulose derivatives grafted with a water-soluble monomer comprising a quaternary ammonium, and disclosed, for example, in U.S. Pat. No. 4,131,576, such as hydroxyalkylcelluloses, for instance hydroxymethyl-, hydroxyethyl- or hydroxypropylcelluloses grafted for instance, with a methacryloyloxyethyltrimethylammonium, methacrylamidopropyltrimethylammonium or dimethyldial-lylammonium salt.

The products sold corresponding to this definition are, for example, the products sold under the name "CELQUAT L 200" and "CELQUAT H 100" by the company National Starch.

The amphoteric fixing polymers that can be used in accordance with the present disclosure include, but are not limited to polymers comprising units B and C distributed randomly in the polymer chain, wherein B is a unit derived from a monomer comprising at least one basic nitrogen atom and C is a unit derived from an acid monomer comprising at least one carboxylic or sulphonic group, or alternatively B and C are groups derived from carboxybetaine or sulphobetaine zwitterionic monomers;

B and C can also be chosen from cationic polymer chains comprising primary, secondary, tertiary or quaternary amine groups, wherein at least one of the amine groups bears a carboxylic or sulphonic group connected via a hydrocarbon group or alternatively B and C form part of a chain of a polymer containing an α,β-dicarboxylic ethylene unit wherein one of the carboxylic groups has been made to react with a polyamine comprising at least one primary or secondary amine group.

According to at least one embodiment of the present disclosure, the amphoteric fixing polymers may be chosen, for example from the following polymers:

(1) copolymers having acidic vinyl units and basic vinyl units, such as those resulting from the copolymerization of a monomer derived from a vinyl compound bearing a carboxylic group such as, acrylic acid, methacrylic acid, maleic acid, α-chloroacrylic acid, and a basic monomer derived from a substituted vinyl compound containing at least one basic atom, such as dialkylaminoalkyl methacrylates and acrylates, dialkylaminoalkylmethacrylamides and -acrylamides. Such compounds are described, for instance, in U.S. Pat. No. 3,836,537;

(2) polymers comprising units derived from:
  a) at least one monomer chosen from acrylamides and methacrylamides substituted on the nitrogen atom with an alkyl group,
  b) at least one acidic comonomer containing at least one reactive carboxylic groups, and
  c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides that may be mentioned in a non-limiting manner include compounds wherein the alkyl groups contain from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example from acrylic acid, methacrylic acid, crotonic acid, itaconic acid, maleic acid and fumaric acid and alkyl monoesters, having 1 to 4 carbon atoms, of maleic or fumaric acids or anhydrides.

The basic comonomers are, in at least one embodiment, chosen from aminoethyl, butylaminoethyl, N,N'-dimethylaminoethyl and N-tert-butylaminoethyl methacrylates.

The copolymers whose CTFA (4th edition, 1991) name is octylacryl-amide/acrylates/butylaminoethyl methacrylate copolymer, such as the products sold under the name AMPHOMER® or LOVOCRYL® 47 by the company National Starch, may also be mentioned in a non-limiting manner.

(3) crosslinked and acylated polyamino amides partially or totally derived from polyamino amides of formula (II):

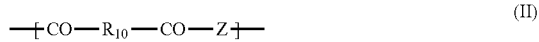 (II)

wherein $R_{10}$ is chosen from divalent groups derived from a saturated dicarboxylic acid, mono- or dicarboxylic aliphatic acids comprising an ethylenic double bond, esters of a lower alkanol, having 1 to 6 carbon atoms, of these acids, and groups derived from the addition of any one of said acids to a bis(primary) or bis(secondary) amine, and Z denotes a group derived from a bis(primary), mono- or bis(secondary) polyalkylene-polyamine and, in at least one embodiment, is chosen from:
  a) in proportions ranging from 60 to 100 mol %, the group:

 (III)

wherein x=2 or 3, and p=2 or 3,
this group being derived from diethylenetriamine, from triethylenetetraamine or from dipropylenetriamine;
  b) in proportions ranging from 0 to 40 mol %, the group (III) above, wherein x=2 and p=1 and which is derived from ethylenediamine, or the group derived from piperazine:

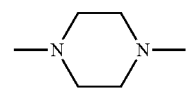

c) in proportions ranging from 0 to 20 mol %, the —NH—$(CH_2)_6$—NH— group being derived from hexamethylenediamine, these polyamino amides being crosslinked by addition reaction of a difunctional crosslinking agents chosen from epihalohydrins, diepoxides, dianhydrides and bis-unsaturated derivatives, using from 0.025 to 0.35 mol of a crosslinking agent per amine group of the polyamino amide and acylated by the action of acrylic acid, chloroacetic acid or an alkane sultone, or salts thereof.

The saturated carboxylic acids are chosen, for example, from acids having 6 to 10 carbon atoms, such as adipic acid, 2,2,4-trimethyladipic acid and 2,4,4-trimethyladipic acid, terephthalic acid, and acids comprising an ethylenic double bond, for example, acrylic acid, methacrylic acid and itaconic acid.

The alkane sultones used in the acylation are chosen from, in at least one embodiment, propane sultone and butane sultone; and the salts of the acylating agents are, in at least one embodiment, chosen from sodium and potassium salts;

(4) polymers comprising zwitterionic units of formula:

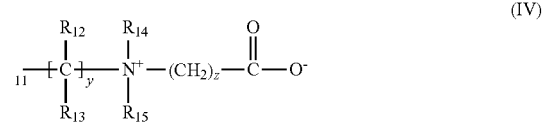 (IV)

wherein $R_{11}$ is chosen from polymerizable unsaturated groups such as acrylate, methacrylate, acrylamide and methacrylamide groups, y and z are integers ranging from 1 to 3, $R_{12}$ and $R_{13}$ are each independently chosen from a hydrogen atom, methyl, ethyl and propyl groups, $R_{14}$ and $R_{15}$ are each independently chosen from a hydrogen atom and alkyl groups, such that the sum of the carbon atoms in $R_{14}$ and $R_{15}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides or vinyl acetate.

By way of example, non-limiting mention may be made of the copolymers of methyl methacrylate/methyl dimethylcarboxymethylammonioethyl methacrylate such as the product sold under the name DIAFORMER Z301 by the company Sandoz;

(5) polymers derived from chitosan comprising monomer units corresponding to the following formulae:

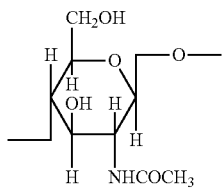

(D)

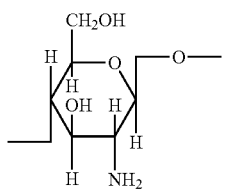

(E)

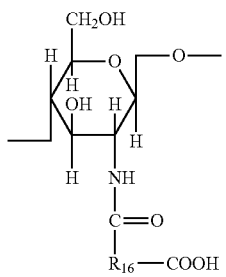

(F)

wherein the unit (D) is present in proportions ranging from 0 to 30%, the unit (E) is present in proportions ranging from 5% to 50% and the unit (F) is present in proportions ranging from 30% to 90%, it being understood that, in this unit (F), $R_{16}$ is chosen from a group of formula:

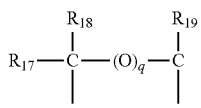

wherein, if q=0, $R_{17}$, $R_{18}$ and $R_{19}$, are each independently chosen from a hydrogen atom, methyl, hydroxyl, acetoxy and amino residues, monoalkylamine residues, and dialkylamine residues that are optionally interrupted by at least one nitrogen atom and/or optionally substituted with at least one group chosen from amine, hydroxyl, carboxyl, alkylthio and sulphonic groups, an alkylthio residue wherein the alkyl group bears an amino residue, at least one of the groups $R_{17}$, $R_{18}$ and $R_{19}$ being, in this case, being a hydrogen atom;

or, if q=1, $R_{17}$, $R_{18}$ and $R_{19}$ are hydrogen atoms, and also the salts formed by these compounds with bases or acids;

(6) Polymers corresponding to general formula (V) are, for example, described in French Patent No. 1 400 366:

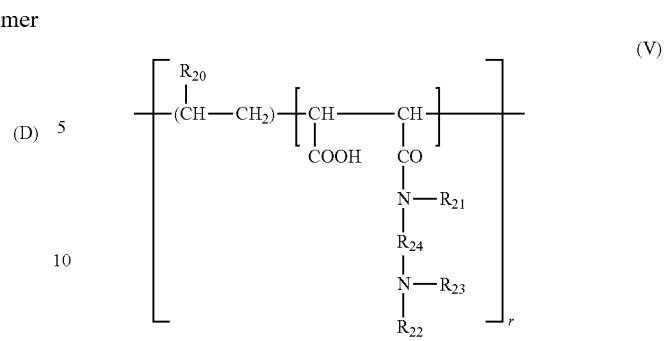

wherein $R_{20}$ is chosen from a hydrogen atom, $CH_3O$, $CH_3CH_2O$ and phenyl groups, $R_{21}$ is chosen from a hydrogen atom and lower alkyl groups, such as methyl or ethyl, $R_{22}$ is chosen from a hydrogen atom, and $C_1$-$C_6$ lower alkyl groups, such as methyl or ethyl, $R_{23}$ is chosen from $C_1$-$C_6$ lower alkyl groups, such as methyl or ethyl or a group corresponding to the formula: —$R_{24}$—$N(R_{22})_2$, wherein $R_{24}$ is chosen from —$CH_2$—$CH_2$—, —$CH_2$—$CH_2$—$CH_2$—, —$CH_2$—, and —$CH(CH_3)$—, and $R_{22}$ having the meanings mentioned above;

(7) polymers derived from the N-carboxyalkylation of chitosan, such as N-carboxymethylchitosan or N-carboxybutylchitosan sold under the name "EVALSAN" by the company Jan Dekker;

(8) amphoteric polymers of the type -D-X-D-X chosen from:

a) polymers obtained by the action of chloroacetic acid or sodium chloroacetate on compounds comprising at least one unit of formula:

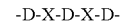 -D-X-D-X-D- (VI)

wherein D is a group

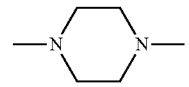

and each instance of X is the symbol E or E', which may be independently chosen from divalent groups, such as an alkylene group with a straight or branched chain comprising up to 7 carbon atoms in the main chain, optionally substituted with at least one hydroxyl group and which can comprise, in addition to oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

 -D-X-D-X— (VI')

wherein D is a group

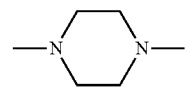

and each instance of X is the symbol E or E' and at least once E'; wherein E has the meaning given above and E' is a divalent group, for example an alkylene group with a straight or branched chain having up to 7 carbon atoms in the main chain, optionally substituted with at least one hydroxyl group and comprising at least one nitrogen atom, the nitrogen atom being substituted with an alkyl chain that is optionally interrupted by an oxygen atom and necessarily comprising at least one carboxyl function or at least one hydroxyl function and betainized by reaction with chloroacetic acid or sodium chloroacetate;

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above, the amphoteric fixing polymers of family (3), such as the copolymers whose CTFA name is octylacryl-amide/acrylates/butylaminoethyl methacrylate copolymer, such as the products sold under the names AMPHOMER®, AMPHOMER® LV 71 or LOVOCRYL® 47 by the company National Starch and those of family (4) such as the copolymers of methyl methacrylate/methyl dimethylcarboxymethylammonioethyl methacrylate, sold, for example, under the name DIAFORMER Z301 by the company Sandoz, are used in at least one embodiment.

The nonionic fixing polymers that may be used according to the present disclosure are chosen, for example, from:
polyalkyloxazolines;
vinyl acetate homopolymers;
vinyl acetate copolymers, for instance copolymers of vinyl acetate and of acrylic ester, copolymers of vinyl acetate and of ethylene, or copolymers of vinyl acetate and of maleic ester, for example of dibutyl maleate;
homopolymers and copolymers of acrylic esters, for instance copolymers of alkyl acrylates and of alkyl methacrylates, such as the products sold by the company Rohm & Haas under the names PRIMAL® AC-261 K and EUDRAGIT® NE 30 D, by the company BASF under the name 8845, or by the company Hoechst under the name APPRETAN® N9212;
copolymers of acrylonitrile and of a nonionic monomer chosen, for example, from butadiene and alkyl (meth)acrylates; mention may be made of the products sold under the name CJ 0601 B by the company Rohm & Haas;
styrene homopolymers;
styrene copolymers, for instance copolymers of styrene and of an alkyl (meth)acrylate, such as the products MOWILITH® LDM 6911, MOWILITH® DM 611 and MOWILITH® LDM 6070 sold by the company Hoechst, and the products RHODOPAS® SD 215 and RHODOPAS® DS 910 sold by the company Rhône-Poulenc; copolymers of styrene, of alkyl methacrylate and of alkyl acrylate; copolymers of styrene and of butadiene; or copolymers of styrene, of butadiene and of vinylpyridine;
polyamides;
vinyllactam homopolymers such as vinylpyrrolidone homopolymers and such as the polyvinylcaprolactam sold under the name LUVISKOL® Plus by the company BASF; and
vinyllactam copolymers such as a poly(vinylpyrrolidone/vinyllactam) copolymer sold under the trade name LUVITEC® VPC 55K65W by the company BASF, poly(vinylpyrrolidone/vinyl acetate) copolymers, such as those sold under the name PVPVA® S630L by the company ISP, LUVISKOL® VA 73, VA 64, VA 55, VA 37 and VA 28 by the company BASF; and poly(vinylpyrrolidone/vinyl acetate/vinyl propionate) terpolymers, for instance the product sold under the name LUVISKOL® VAP 343 by the company BASF.

The alkyl groups of the nonionic polymers mentioned above comprise, in at least one embodiment, from 1 to 6 carbon atoms.

According to the present disclosure, it is also possible to use fixing polymers of grafted silicone type comprising a polysiloxane portion and a portion consisting of a nonsilicone organic chain, wherein one of the two portions constitutes the main chain of the polymer, and the other is grafted onto said main chain.

These polymers are described, for example, in European Patent Application Nos. EP-A-0 412 704, EP-A-0 412 707, EP-A-0 640 105, and EP-A-0 582 152, and International Patent Application Publication Nos. WO 95/00578, and WO 93/23009 and U.S. Pat. Nos. 4,693,935, 4,728,571 and 4,972,037.

These polymers may be amphoteric, anionic or nonionic, and are, in at least one embodiment, chosen from anionic and nonionic polymers.

Such polymers are, for example, copolymers that can be obtained by free radical polymerization from the monomer mixture formed from:
a) 50 to 90% by weight of tert-butyl acrylate;
b) 0 to 40% by weight of acrylic acid;
c) 5 to 40% by weight of a silicone macromer of formula:

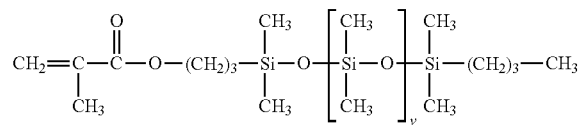

wherein v is a number ranging from 5 to 700, and the weight percentages are calculated relative to the total weight of the monomers.

Other examples of grafted silicone polymers are, for example, polydimethylsiloxanes (PDMSs) onto which are grafted, via a thiopropylene-type connecting chain, mixed polymer units of the poly(meth)acrylic acid type and of the polyalkyl (meth)acrylate type and polydimethylsiloxanes (PDMSs) onto which are grafted, via a thiopropylene-type connecting chain, polymer units of the polyisobutyl (meth) acrylate type.

Another type of silicone fixing polymer that may be mentioned is the product LUVIFLEX® Silk, sold by the company BASF.

Functionalized or non-functionalized, silicone or non-silicone, cationic, nonionic, anionic or amphoteric polyurethanes or mixtures thereof may also be used as fixing polymers in accordance with the present disclosure.

Non-limiting mention of suitable polyurethanes that may be included are those disclosed in European Patent Application Nos. EP 0 751 162, EP 0 637 600, EP 0 648 485, EP 0 619 111 and EP 0 656 021, and French Patent No. FR 2 743 297, and International Patent Application Publication No. WO 94/03510.

Other useful polyurethanes include, but are not limited to the products sold under the names LUVISET PUR® and LUVISET® SI PUR by the company BASF.

The concentration of fixing polymer(s) used in the compositions according to the present disclosure, ranges from 0.1% to 20%, such as ranging from 0.5% to 10% by weight relative to the total weight of the composition.

The compositions according to the present disclosure may be in any of the forms suitable for topical application, such as in the form of solutions of the lotion or serum type; in the form of aqueous gels; in the form of emulsions obtained by dispersion of a fatty phase in an aqueous phase (O/W) or vice versa (W/O), in the form of milks or creams; in the form of a mousse, of waxes or of pastes, or in the form of a spray or of an aerosol.

When xanthan gum is used as the at least one microbial gum, the composition will, in at least one embodiment, be formulated as a cream-gel.

When the composition according to the present disclosure is packaged in an aerosol device, it comprises at least one propellant chosen from volatile hydrocarbons, such as N-butane, propane, isobutane, pentane, halogenated hydrocarbons, carbon dioxide, nitrous oxide, dimethyl ether (DME), nitrogen, compressed air. In at least one embodiment, dimethyl ether is used.

The at least one propellant is present in the composition in a total amount ranging from 5% to 90% by weight relative to the total weight of the composition in the aerosol device, such as ranging from 10% to 60% by weight relative to the total weight of the composition in the aerosol device.

The composition according to the present disclosure may, for instance, be used as a leave-in application to the hair.

The at least one alkoxysilane comprising least one basic functional group, and the at least one microbial gum may also be formulated separately and mixed just before application; they may be packaged in a two-compartment (bicompartmental) device, they may also be formulated separately and applied, to the hair, one after the other.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following examples serve to illustrate embodiments of the present disclosure without, however, exhibiting a limiting nature.

EXAMPLES

The following compositions were prepared:

The concentrations are expressed in grams of active materials per 100 grams of composition.

Formulation Examples

Example 1: Styling Cream-Gel

| | |
|---|---|
| Aminopropyltriethoxysilane (Dow Corning) | 10% a.m. |
| HCl | qs pH = 10.5 |
| KELTROLT (CP Kelco) | 2% a.m. |
| Water | qs 100% |

Example 2: Styling Gel in a Bicompartmental Device

Compartment A:

| | |
|---|---|
| Aminopropyltriethoxysilane (Dow Corning) | 10% a.m. |
| HCl | qs pH = 10.5 |
| JAGUAR HP105 (Rhodia) | 1.5% a.m. |
| Demineralised water | qs 100% |

Compartment B:

| | |
|---|---|
| KELTROLT (CP Kelco) | 2% a.m. |
| Water | qs 100% |

The contents of the 2 compartments were mixed on leaving the device.

Example 3: Styling Gel in a Bicompartmental Device

Compartment A:

| | |
|---|---|
| N-(2-Aminoethyl)aminomethylphenethyl-trimethoxysilane (Gelest) | 10% a.m. |
| KLUCEL G from Aqualon-Hercules (hydroxypropyl cellulose) | 2% |
| Ethanol | 50% |
| Demineralised water | qs 100% |

Compartment B:

| | |
|---|---|
| KELTROL T (CP Kelco) | 2% a.m. |
| Water | qs 100% |

The contents of the 2 compartments were mixed on leaving the device.

Application:

The products were applied to wet hair and left to dry in the open air, by blow-drying, and by using flat tongs, respectively.

Results:

On damaged (bleached) hair: styling and care effects (body, manageability, soft and smooth feel) withstood several shampooings.

On dry, curly hair: volume control, curl shape control and care effects (soft and smooth feel) withstood several shampooings.

What is claimed is:

1. A nondetergent cosmetic composition comprising:
   at least one cosmetically acceptable medium,
   at least one alkoxysilane having at least one basic functional group chosen from the compounds of formula (I):

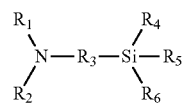

wherein:
R₁ and R₂ are each independently chosen from a hydrogen atom or ethyl, propyl, or aminoethyl groups,
R₃ is chosen from ethyl, propyl, or methylphenethyl groups, and
R₄, R₅ and R₆, are each independently chosen from methyl, methoxy or ethoxy groups; and
at least one microbial gum;
wherein the at least one alkoxysilane having at least one basic functional group is present in an amount ranging from 0.1% to 15%, by weight of the total weight of the composition, and
wherein the weight ratio between the at least one microbial gum and the at least one alkoxysilane comprising at least one basic functional group is greater than or equal to 1/20.

2. The nondetergent cosmetic composition according to claim 1, wherein the at least one alkoxysilane comprising at least one basic functional group is chosen from 3-aminopropyltriethoxysilane, 3-aminoethyltriethoxysilane, 3-aminopropylmethyldiethoxysilane, N-(2-aminoethyl)-3-aminopropyltriethoxysilane and N-(2-aminoethylaminomethyl)phenethyltrimethoxysilane.

3. The nondetergent cosmetic composition according to claim 1, wherein the at least one microbial gum is chosen from sclerotium gums, gellan gums, pullulan gums, curdlan gums, xanthan gums, grifolan gums, lentinan gums, schizophyllan gums, spirulinan gums and krestin gums.

4. The nondetergent cosmetic composition according to claim 3, wherein the at least one microbial gum is chosen from sclerotium gums and xanthan gums.

5. The nondetergent cosmetic composition according to claim 1, wherein the at least one microbial gum is present in the composition in a total amount ranging from 0.01% to 10% by weight of the total weight of the composition.

6. The nondetergent cosmetic composition according to claim 1, wherein the weight ratio between the at least one microbial gum and the at least one alkoxysilane comprising at least one basic functional group ranges from 1/20 to 1/3.

7. The non detergent cosmetic composition according to claim 1, wherein the at least one cosmetically acceptable medium is aqueous or aqueous-alcoholic.

8. The nondetergent cosmetic composition according to claim 1, further comprising at least one additional thickener different from the at least one microbial gum, chosen from carboxyvinyl polymers and copolymers, (alkyl)acrylic polymers and copolymers, (alkyl)acrylamide polymers and copolymers, poly(oxyalkylene) glycols, poly(oxyalkylene) glycol esters, hydroxyalkylcelluloses, alginates, natural gums, carrageenans, and clays.

9. The nondetergent cosmetic composition according to claim 1, further comprising at least one surfactant chosen from anionic, nonionic, amphoteric and cationic surfactants.

10. The nondetergent cosmetic composition according to claim 1, further comprising at least one additive chosen from fixing polymers, silicones and fatty substances.

11. A method for treatment of keratin materials, comprising applying to the keratin materials, a nondetergent cosmetic composition comprising:
at least one cosmetically acceptable medium,
at least one alkoxysilane having at least one basic functional group chosen from the compounds of formula (I):

wherein:
R₁ and R₂ are each independently chosen from a hydrogen atom or ethyl, propyl, or aminoethyl groups,
R₃ is chosen from ethyl, propyl, or methylphenethyl groups, and
R₄, R₅ and R₆, are each independently chosen from methyl, methoxy or ethoxy groups, and
at least one microbial gum;
wherein the at least one alkoxysilane having at least one basic functional group is present in an amount ranging from 0.1% to 15%, by weight of the total weight of the composition, and
wherein the weight ratio between the at least one microbial gum and the at least one alkoxysilane comprising at least one basic functional group is greater than or equal to 1/20.

12. A method for hair shaping comprising
applying to the hair, a nondetergent cosmetic composition comprising:
at least one cosmetically acceptable medium,
at least one alkoxysilane having at least one basic functional group chosen from the compounds of formula (I):

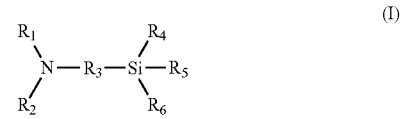

wherein:
R₁ and R₂ are each independently chosen from a hydrogen atom or ethyl, propyl, or aminoethyl groups,
R₃ is chosen from ethyl, propyl, or methylphenethyl groups, and
R₄, R₅ and R₆, are each independently chosen from methyl, methoxy or ethoxy groups, and
at least one microbial gum;
wherein the at least one alkoxysilane having at least one basic functional group is present in an amount ranging from 0.1% to 15%, by weight of the total weight of the composition, and
wherein the weight ratio between the at least one microbial gum and the at least one alkoxysilane comprising at least one basic functional group is greater than or equal to 1/20; and
physically shaping the hair.

13. The nondetergent cosmetic composition according to claim 1, wherein the at least one alkoxysilane comprising at least one basic functional group is present in a total amount ranging from 1% to 15% by weight of the total weight of the composition.

14. The nondetergent cosmetic composition according to claim 5, wherein the at least one microbial gum is present in the composition in a total amount ranging from 0.1% to 4% by weight of the total weight of the composition.

15. The method according to claim 11, wherein the keratin materials are chosen from hair that is damaged, curly, dry or fine.

* * * * *